United States Patent [19]
Swanson et al.

[11] Patent Number: 5,634,938
[45] Date of Patent: Jun. 3, 1997

[54] DEFIBRILLATOR WAVEFORM GENERATOR FOR GENERATING WAVEFORM OF LONG DURATION

[75] Inventors: David K. Swanson, Roseville; James P. Nelson, Shoreview; Douglas J. Lang, Arden Hills, all of Minn.

[73] Assignee: Cardiac Pacemakers, Inc., St. Paul, Minn.

[21] Appl. No.: 547,845

[22] Filed: Oct. 25, 1995

Related U.S. Application Data

[63] Continuation of Ser. No. 203,737, Feb. 28, 1994, abandoned, which is a continuation of Ser. No. 827,215, Jan. 30, 1992, abandoned.

[51] Int. Cl.$^6$ ............................................. A61N 1/39
[52] U.S. Cl. ................................. 607/5; 607/7; 607/74
[58] Field of Search ........................... 607/5, 4, 68, 72, 607/74, 7

[56] References Cited

U.S. PATENT DOCUMENTS

| | | |
|---|---|---|
| 4,375,817 | 3/1983 | Engle et al. . |
| 4,548,203 | 10/1985 | Tacker, Jr. et al. . |
| 4,800,883 | 1/1989 | Winstrom . |
| 4,821,723 | 4/1989 | Baker, Jr. et al. . |
| 4,953,551 | 9/1990 | Mehra et al. . |
| 5,199,429 | 4/1993 | Kroll et al. . |

FOREIGN PATENT DOCUMENTS

| | | |
|---|---|---|
| 277739/89 | 7/1989 | Australia . |
| 0280526 | 8/1988 | European Pat. Off. . |
| 0218219 | 9/1988 | European Pat. Off. . |
| 0326690 | 8/1989 | European Pat. Off. . |
| 0515059 | 11/1992 | European Pat. Off. . |
| 1317369 | 3/1964 | France . |

OTHER PUBLICATIONS

Tang, et al., "Ventricular Defibrillation Using Biphasic Waveforms: The Importance of Phasic Duration", Biphasic Waveforms for Defibrillation, 207–214 (1989).

Jones, et al., "Increasing Fibrillation Duration Enhances Relative Asymmetrical Biphasic Versus Monophasic Defibrillator Waveform Efficacy", Circulation and Research, 376–384 (1990).

Wessale, et al., "Bipolar Catheter Defibrillation in Dogs Using Trapezoidal Waveforms of Various Tilts", Catheter Defibrillation with Trapezoidal Waveforms, 359–365 (1980).

Irnich, "The Chronaxie Time and Its Practical Importance", The Chronaxie Time and Its Practical Importance, 292–301 (1980).

Feeser, et al., "Strength–Duration and Probability of Success Curves for Defibrillation With Biphasic Waveforms", Success Curves for Defibrillation, 2128–2141 (1990).

Winkle, et al., "Improved low energy defibrillation efficacy in man with the use of biphasic truncated exponential waveform", Biphasic waveform defibrillation in man, 122–127 (1989).

Koning, et al., "Amplitude–duration relation for direct ventricular defibrillation with rectangular current pulses*", Medical and Biological Engineering, 388–395 (1975.

Chapman, et al., "Strength–Duration Curves of Fixed Pulse Width Variable Tilt Truncated Exponential Waveforms for Non–thoracomy Internal Defibrillation in Dogs", 1045–1050 (1988).

(List continued on next page.)

*Primary Examiner*—Jeffrey R. Jastrzab
*Attorney, Agent, or Firm*—Barnes & Thornburg

[57] ABSTRACT

An implantable defibrillator/cardioverter which generates a biphasic waveform having a duration of at least 15–80 msec and a small "tilt" between the leading edge and trailing edge voltages of each phase. In one embodiment, two capacitors are connected in parallel to create an effectively large capacitance to generate a slowly decaying waveform. In another embodiment, a high capacitance bipolar capacitor is used, which capacitance is at least 200 microFarads.

8 Claims, 6 Drawing Sheets

OTHER PUBLICATIONS

Bardy, et al., "A Prospective Randomized Evaluation of Biphasic Versus Monophasic Waveform Pulses on Defibillation Efficacy in Humans", Biphasic Versus Monophasic Defibrillation, 728–33, (1989).

Kavanagh, et al., "Comparison of the Internal Defibrillation Thresholds for Monophasic and Double and Single Capacitor Biphasic Waveforms", Monophasic, Double and Single Capacitor Waveforms, 1343–1349 (1989).

McDaniel, et al., Optimal Biphasic Waveform Duration for Canine Cardiac Defibrillation with a "Single Capacitor" Waveform and a Non–Thoractomy Electrode System, Annual International Conference of the IEEE Engineering in Medicine and Biology Society, vol. 12, No. 2, 1990, pp. 636–637.

Lang, et al., Strength–Duration Relationship for Biphasic Defibrillation in Dogs, IEEE Engineering in Medicine & Biology Society 11th Annual International Conference, Ventricular Defibrillation, 1989, pp. 80–81.

McDaniel, et al., An Up–Down Algorithm for Estimation of the Cardiac Ventricular Defibrillation Threshold, Medical Instrumentation, 1988, vol. 22, No. 8, pp. 286–292.

Eaton, Multivariate Statistics: A Vector Space Approach, New York, John Wiley & Sons, Inc., 1983, pp. 150–154.

Chatfield, Statistics for Technology, London, Chapman and Hall, 1975, pp. 121–125.

Dixon, The Up–Down Method for Small Samples, J Am Stat. Assoc., 1965: 60:967–978.

Weiss, Sur La Possibilite De Rendre Comparables Entre Eux Les Appareils Servant A L'Excitation Electrique, Arch Ital Biol, Turin, Hermann Loescher 1901; 35:413–446.

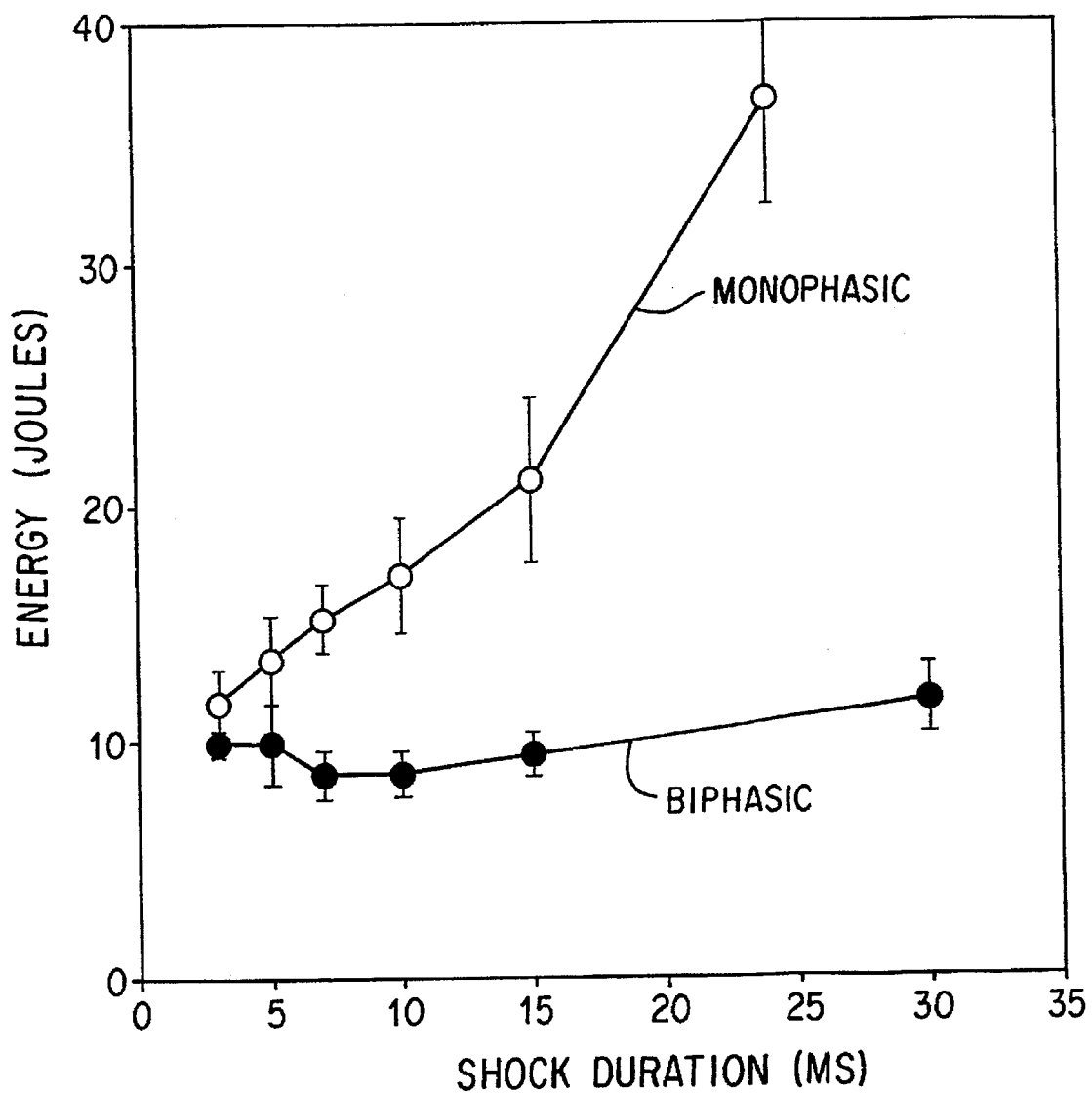
F I G. 1

DEFIBRILLATOR WAVEFORM GENERATOR FOR GENERATING WAVEFORM OF LONG DURATION

This is a continuation application of Ser. No. 08/203,737, filed on Feb. 28, 1994, now abandoned, which is a continuation of Ser. No. 07/827,215, filed Jan. 30, 1992, now abandoned.

RELATED APPLICATION

This application is related to U.S. patent application Ser. No. 07/828,136, filed on the same day as this application, and entitled "DUAL CAPACITOR BIPHASIC DEFIBRILLATOR WAVEFORM GENERATOR EMPLOYING SELECTIVE CONNECTION OF CAPACITORS FOR EACH PHASE" now U.S. Pat. No. 5,411,525.

BACKGROUND OF THE INVENTION

The present invention relates to cardiac defibrillation, and more particularly to a defibrillation system including a pulse generator which generates a long duration defibrillation waveform.

When used hereinafter, the term "defibrillation" is meant to include high energy defibrillation and lower energy cardioversion.

Present defibrillation devices generate and deliver a truncated exponential waveform with a duration less than 12 msec, or some variation thereof. According to conventional wisdom, the use of defibrillation waveforms with durations 15-20 msec or longer would be counter-indicated for defibrillation. In particular, it has been the assumption by experts in the field that the strength-duration relationship of a biphasic waveform are the same as for a monophasic waveform. That is, it is the general consensus that increasing waveform duration prohibitively increases the necessary energy requirements.

In the last five years, there have been several reports of human and animal studies showing that some biphasic waveforms are more efficacious than monophasic waveforms. See Jones et al., "Increasing Fibrillation Duration Enhances Relative Asymmetric Biphasic Versus Monophasic Defibrillator Waveform Efficacy", *Circulation and Respiration*, 376–384, Vol. 67 (1990); Bardy et al, "A Prospective Randomized Evaluation of Bipolar Versus Monopolar Waveform Pulses on Defibrillation Efficacy in Humans", *Journal of the American College of Cardiology*, 728–733, Vol. 14 (1989); and Winkle et al., "Improved Low Energy Defibrillation Efficacy in Man With the Use of a Biphasic Truncated Exponential Waveform", *American Heart Journal*, 122–127, Vol. 117 (1989). These articles describe a ratio of energy requirements of a biphasic waveform as compared to the monophasic waveform that is less than 1.0. None of these articles indicate that ratio may be dependent on waveform duration.

The present generation of defibrillators have, to a large extent, been designed using strength-duration data determined with monophasic waveforms. When monophasic truncated exponential waveforms are used, defibrillation waveforms with long pulse durations (>10 msec) have no advantages over shorter duration waveforms.

Therefore, manufacturers of implantable defibrillator devices have used output capacitors with a capacitance of 60 to 150 microFarads and waveform durations less than 15 msec, and typically less than 10 msec. Waveform durations have been maintained substantially the same as manufacturers have changed their defibrillator designs to produce biphasic defibrillation shocks.

Recent patents further demonstrate that state-of-the-art defibrillation waveforms have durations shorter than 15 msec. See, for example, U.S. Pat. Nos. 4,548,203 to Tacker, Jr. et al., 4,953,551 to Mehra et al., and 4,821,723 to Baker et al.

It is known that the pulse duration has a major impact on the strength requirements for stimulating tissue. Since most theories of defibrillation involve stimulation of refractory tissue, one would expect the strength-duration relationship for defibrillation to be at least qualitatively similar to that of pacing. This has been born out by studies by Wassale et al. and Konig et al. and described in their respective articles "Bipolar Catheter Defibrillation in Dogs Using Trapezoidal Waveforms of Various Tilts", *Journal of Electrocardiology*, 359–366, Vol. 13 (1980), hereinafter "Wassale et al."; and "Amplitude-Duration Relationship for Direct Ventricular Defibrillation with Rectangular Current Pulses", *Medical Biological Engineering*, 388–395, Vol. 13 (1975), hereinafter "Konig et al.". The overall shape of the strength-duration curves for defibrillation with both monophasic truncated exponential and rectangular waveforms are similar to those determined for pacing. However, the pulse durations that minimize energy delivery requirements are lower for pacing (0.5 msec) as described by Irnich in the article "The Chronaxie Time and Its Practical Importance", *PACE*, 292–301, Vol. 3 (1980), hereinafter "Irnich", than for defibrillation (4 msec) as described by Wassale et al.

Defibrillation with monophasic waveforms appears to follow a hyperbolic strength-duration relationship, as does pacing. Defibrillation strength requirements have been measured for rectangular waveforms of different durations (1, 2, 5, 10, 20, 30 and 40 msec). See Konig et al. A good fit was found between their current amplitude data and a hyperbolic strength-duration curve with a chronaxie (a duration that gives minimum energy) at about 4 msec. In the aforementioned article by Wassale et al., strength-duration curves for monophasic truncated exponential waveforms were determined for several different tilts. Current requirements for these trapezoidal waveforms also increased as shock duration decreased, but shock energy was minimized at 2 to 4 msec, depending on the tilt. Both studies show a strength-duration relationship for defibrillation that is similar to that seen in pacing. However, it was found by Irnich that the chronaxie for pacing with rectangular waveforms is about 0.5 msec, while the chronaxie for defibrillation with monophasic waveforms is about 4 msec.

In an article by Chapman et al. entitled "Strength-Duration Curves of Fixed Pulse Width Variable Tilt Truncated Exponential Waveforms for Nonthoracotomy Internal Defibrillation in Dogs", *PACE*, 1045–1050, Vol. 11 (1988), the curve of delivered energy requirements versus pulse width for delivered energy is described for single-capacitor monophasic waveforms (exponential with fixed time constants). Energy requirements increased monotonically by only 50% as duration was increased from 2.5 to 15 msec, then increased dramatically for pulses of 20 msec durations. Energy requirements for the 20 msec pulse were 1.5 times that of the energy required for 15 msec pulses.

Feeser et al., in their article entitled "Strength-Duration and Probability of Success Curves for Defibrillation With Biphasic Waveforms", *Circulation*, 2128–2141, Vol. 82 (1990), showed that for at least some biphasic waveforms, extending waveform durations to more than 15 msec dramatically increases energy requirements. However, unlike our experiments described below, tilt was not held constant in any of their experiments. In the study described by Feeser et al., trailing edges for long waveforms were sometimes very low. MacDaniel et al., in their article entitled "Optimal Biphasic Duration for Canine Defibrillation with a 'Single Capacitor' Waveform and a Non-Thoracotomy Electrode System", Annual Conference of IEEE EMBS, 1990, Volume 12, pages 636–637, showed that, for monophasic pulses of long duration, low trailing voltages are disadvantageous.

It has previously been shown that for fixed-duration shocks, the effectiveness of the truncated biphasic waveforms is critically dependent on the exact shape of the waveform. MacDaniel et al. and Feeser et al. have shown that for single capacitor waveforms, defibrillation shock efficacy varies as the ratio of the durations of the first and second phases is changed. Biphasic waveforms with first or second phases of short duration are actually less efficacious than monophasic pulses.

The strength-duration curves we found for the type of biphasic waveforms used are very different from those previously determined for truncated monophasic waveforms. The strength-duration relationship for energy requirements with biphasic truncated exponential waveforms were relatively flat and may greatly improve implantable defibrillator designs. Specifically, we discovered that defibrillation with long biphasic defibrillation pulses (20 msec) requires significantly lower peak voltages, with almost no increase in energy requirements.

Animal studies involving the present invention studied the effect of waveform duration on defibrillation efficacy of a biphasic truncated exponential waveform in six pigs. In each pig, defibrillation success curves were determined for waveform durations of 3, 5, 7, 10, 15 and 30 msec. The waveform shape chosen was of the "single capacitor" type with the trailing edge of the first pulse equal in magnitude to the leading edge of the second. The first pulse terminated at 40%, and the second pulse at 20% of the initial voltage of the first pulse, with the time constants of each phase being equal.

The effect of waveform duration on defibrillation efficacy of a monophasic truncated exponential waveform was determined in an additional six pigs. Waveform durations were the same as with the biphasic waveform, except the longest duration tested was 24 msec rather than 30 msec. The monophasic waveform terminated at 40% of the initial voltage.

All shocking electrodes were placed by fluoroscopy. One 11 F 3.4 cm long coil was positioned in the right ventricle and another coil of the same dimension was located in the high right atrium. A subcutaneous wire array electrode (100 cm$^2$) was positioned such that the image of the right ventricular shocking coil and the subcutaneous electrode coincided in a lateral view. Thoracic X-ray films were made to verify correct placement of both shocking catheters and the subcutaneous electrode.

Fibrillation was allowed to run for 15 seconds after induction with a 9 volt DC signal between an endocardial sensing lead and an indifferent electrode. Then defibrillation was attempted with a defibrillator designed for research using a shock of the selected waveform duration. Rescue monophasic transthoracic defibrillation shocks were given with an external defibrillator (about 100 J) through an electrode pad on the right thorax and the subcutaneous electrode on the left. Only the initial shock of each fibrillation episode was used to evaluate defibrillation efficacy. The energy requirements for defibrillation were measured for the six waveform durations with the shocks being delivered according to an interleaved up/down protocol (described below). A total of 15 shocks were delivered by this protocol for each of the six durations (a total of 90 shocks). Data from these shocks were used to determine probability-of-success curves for each waveform duration.

TABLE I

Peak Current Amplitudes of First Shocks For Waveforms of Indicated Duration

| Biphasic | | Monophasic | |
| --- | --- | --- | --- |
| Duration | Peak I (Amp) | Duration | Peak I (Amp) |
| 3 | 22.5 | 3 | 22.5 |
| 5 | 13.3 | 5 | 12.0 |
| 7 | 10.0 | 7 | 12.0 |
| 10 | 7.8 | 10 | 12.0 |
| 15 | 7.0 | 15 | 12.0 |
| 30 | 6.3 | 24 | 12.0 |

Table I above shows the peak delivered current for the initial shock given for each of the six waveform durations. It should be noted that the current levels for first shocks were different for the monophasic and biphasic waveforms. For all succeeding shocks, the peak current and success of the immediately preceding shock with that waveform duration determined the peak current selected. If the prior shock at that waveform duration failed, then the peak current was increased by one step; for a successful shock, the peak current was decreased by one step. Initial current step sizes were 20%; at the first reversal, the step size was decreased to 10%.

The interleaving protocol was carried out as follows. The six durations were arranged in random order, then the first test shocks for each duration were delivered in that random order. The order was again randomized, and the second test shock for each duration were delivered according to the new order. That process was continued with 15 separate randomizations of order used, one for each of the 15 shocks delivered for each shock duration. This methodology ensured that, for example, the tenth shock given at one duration always preceded the eleventh shock given at another duration.

Pulse width and initial current were selected by the protocol described above. These values, plus the measured energy and voltage were recorded for each shock. Two minutes separated each fibrillation-defibrillation episode, unless more time was required for the animal to return to basal conditions as indicated by surface or endocardial ECG's, or blood pressure measurements.

For each pulse duration, two parameter probability-of-success curves (mid-point and width) were determined for delivered energy, peak voltage and current. To produce the sigmoid defibrillation success curves, modified error functions were fitted to the data of conversion success or failure for each measured value using the maximum likelihood method. For each pulse duration, the energies, voltages and currents at which the percent probabilities for defibrillation success equaled 50% ($E_{50}$, $V_{50}$ and $I_{50}$) and 80% ($E_{80}$, $V_{80}$ and $I_{80}$) were determined from the success curves.

As shown in FIG. 1, for the biphasic waveform, it was found that shock duration had no statistically significant effect on energy requirements over the range of 3 to 15 msec. Energy requirements were increased about 25% for shock durations of 30 msec. For the monophasic waveform as shown in FIG. 1, defibrillation energy requirements increased monotonically as shock durations were increased from 3 to 24 msec. The $E_{50}$ for shocks 3 msec long was 11.6±3.1 joules compared to 36.8±9.7 joules for shocks 24 msec long.

For the biphasic waveforms, it was found that current and voltage requirements declined monotonically with increases in waveform duration as shown in FIG. 2. Peak current and voltage requirements were 2.5 times higher for waveform durations of 3 msec than for durations of 30 msec. For the monophasic waveforms, current and voltage requirements declined significantly as shock durations were increased from 3 to 10 msec as shown in FIG. 3. There was no significant further decreases as the durations were set at 15 and 24 msec, respectively.

SUMMARY OF THE INVENTION

It is a primary object of the present invention to provide a defibrillator which is capable of generating an effective defibrillation waveform with minimal electrical energy supply requirements.

It is another object of the present invention to provide a defibrillator which defibrillates the heart with lower peak voltages.

It is yet another object of the present invention to provide a defibrillator which defibrillates the heart with a long duration biphasic waveform having lower peak voltage.

It is yet another object of the present invention to provide a defibrillator which defibrillates/cardioverts with lower peak voltages so as to minimize both tissue stunning and post-shock depression of local electrograms.

It is still another object of the present invention to provide a pulse generator for a defibrillator including a low leakage, high-valued capacitor for generating a defibrillation waveform.

The present invention relates to a pulse generator for a defibrillator/cardioverter which generates a defibrillation waveform with less voltage and current requirements. In a first embodiment, the pulse generator comprises two capacitors connected in parallel. The capacitors are discharged to generate a biphasic waveform. In a second embodiment, a single large value, low leakage bipolar capacitor is used.

It is a further object of the present invention to provide a defibrillation shock waveform with an overall duration of 15 msec to 80 msec. From our animal experiments, we expect to substantially reduce current and voltage requirements with such waveforms in external and implantable defibrillation systems.

There are several advantages to a defibrillation waveform requiring lower peak voltages. First, tissue stunning, heart block and heart dysfunction are minimized. Second, the pulse generator output circuitry may be simplified and have greater reliability.

The above and other objects and advantages will become more readily apparent when reference is made to the following description taken in conjunction with the accompanying drawings.

BRIEF DESCRIPTION OF THE DRAWINGS

FIG. 1 is a graph illustrating energy versus duration relationships for monophasic and biphasic waveforms determined from animal studies.

DETAILED DESCRIPTION OF THE DRAWINGS

FIG. 1 illustrates the strength-duration relationships for delivered energy of a constant-tilt biphasic waveform and of a constant-tilt monophasic truncated exponential waveform. The data from this graph were obtained from two series of pig experiments, the details of which are described above. Energy requirements were significantly lower for the biphasic waveform at all durations tested above 5 msec. It is quite evident from this figure that the relative benefit of the biphasic waveform is very dependent on waveform duration. For durations of 3 or 5 msec, the energy advantage for the biphasic waveform is small. However, for the durations used according to the present invention, the biphasic energy requirements are several-fold lower than the monophasic waveform. It should also be noted that the strength-duration curve for energy of the biphasic waveform is quite flat over waveform durations of 3 to 30 msec.

Figure 2:
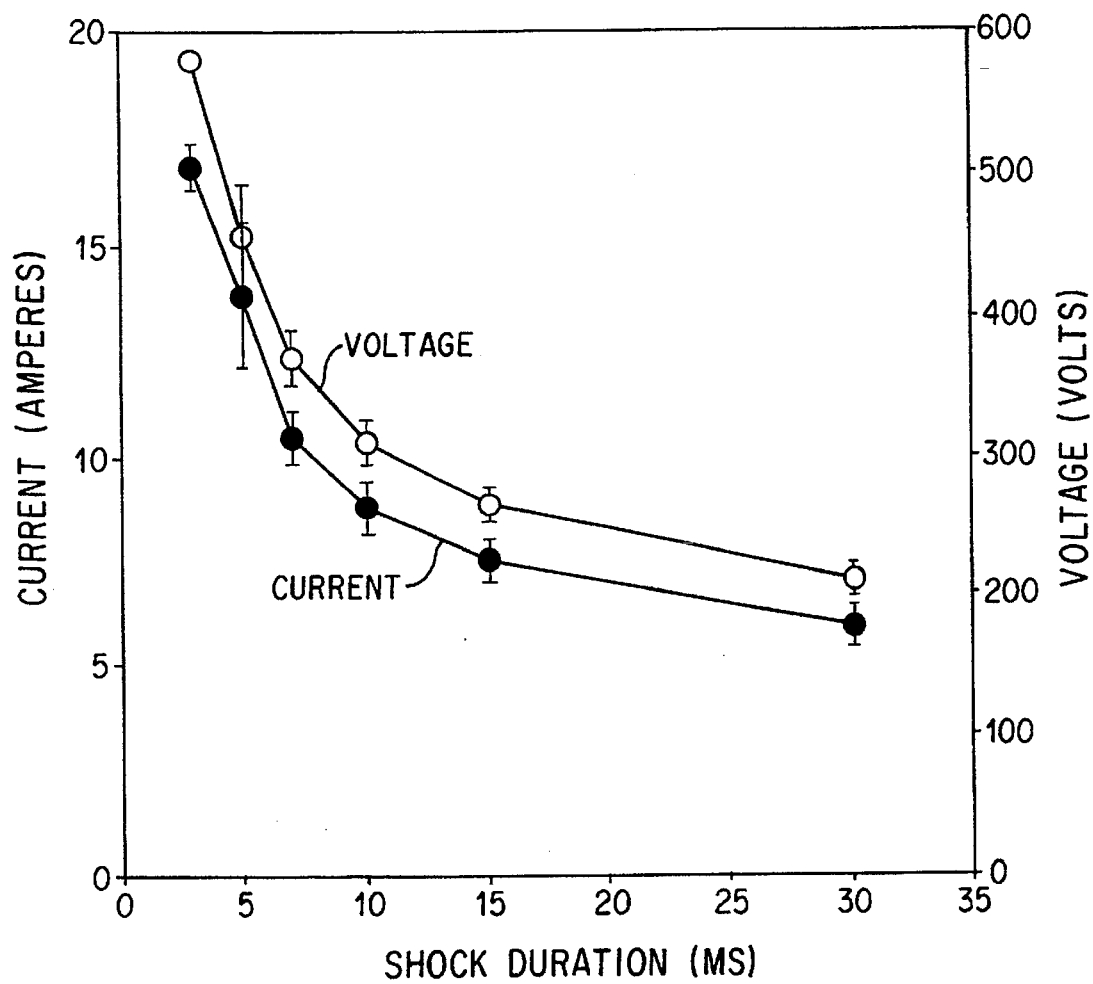
FIG. 2 is a graph illustrating voltage and current versus duration relationships for biphasic waveforms determined from animal studies.
Figure 3:
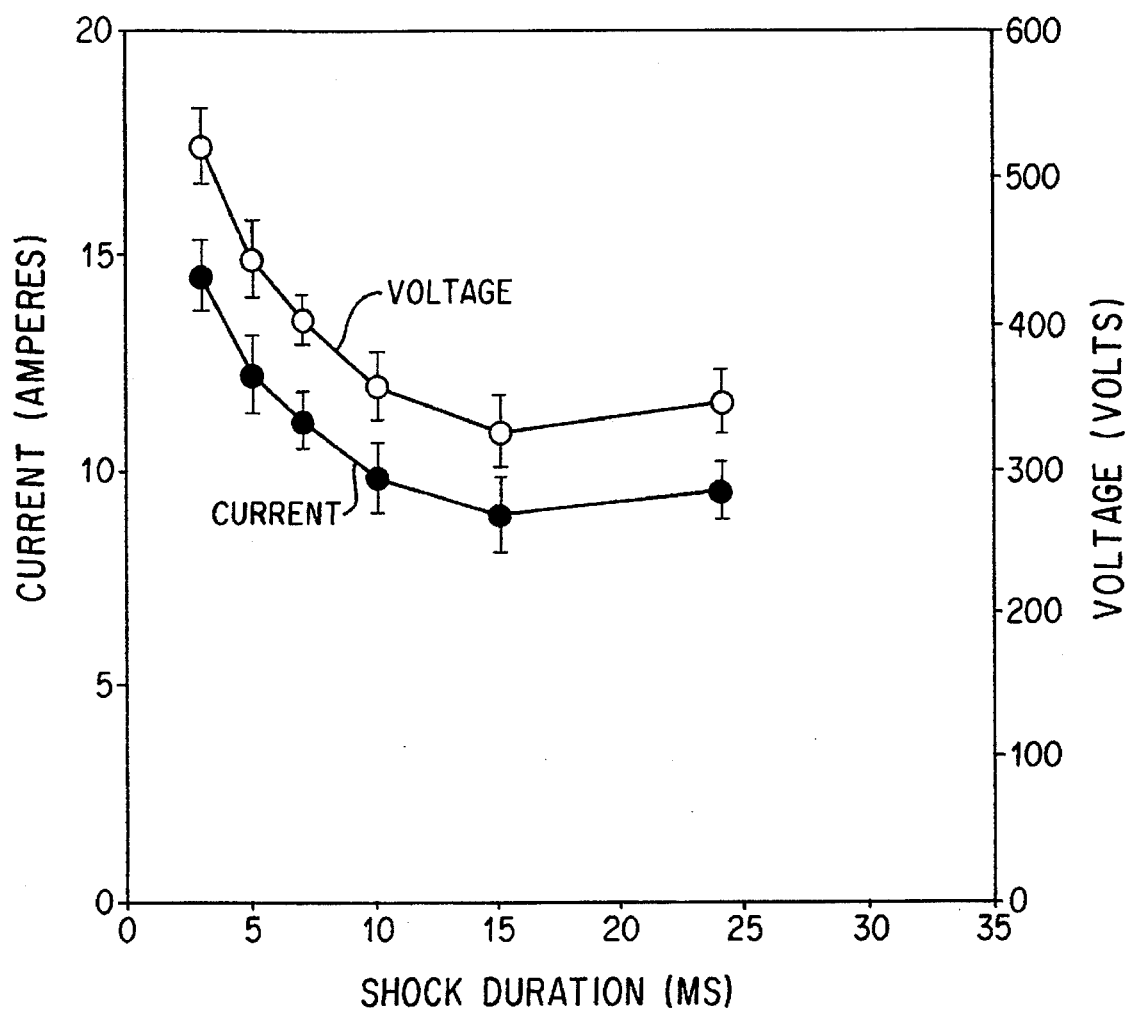
FIG. 3 is a graph illustrating voltage and current versus duration relationships for monophasic waveforms determined from animal studies.

FIGS. 2 and 3 illustrate the strength-duration relationships for peak voltage and current requirements for constant-tilt biphasic and monophasic waveforms, respectively. The data from these graphs were obtained from two series of pig experiments, the details of which are described above. FIG. 2 shows that for the constant-tilt biphasic waveform, peak voltage and current requirements decrease monotonically with increases in duration for pulse durations of 3 to 30 msec. A comparison of FIG. 1 and 2 shows that peak voltage and current can be decreased substantially, with almost no penalty in increased energy requirements, if a biphasic waveform with long duration (greater than 15 msec) is used. In contrast, for the monophasic waveform, no significant changes in peak voltage and current requirements were observed as waveform duration was increased from 10 to 24 msec (FIG. 3).

Figure 4:
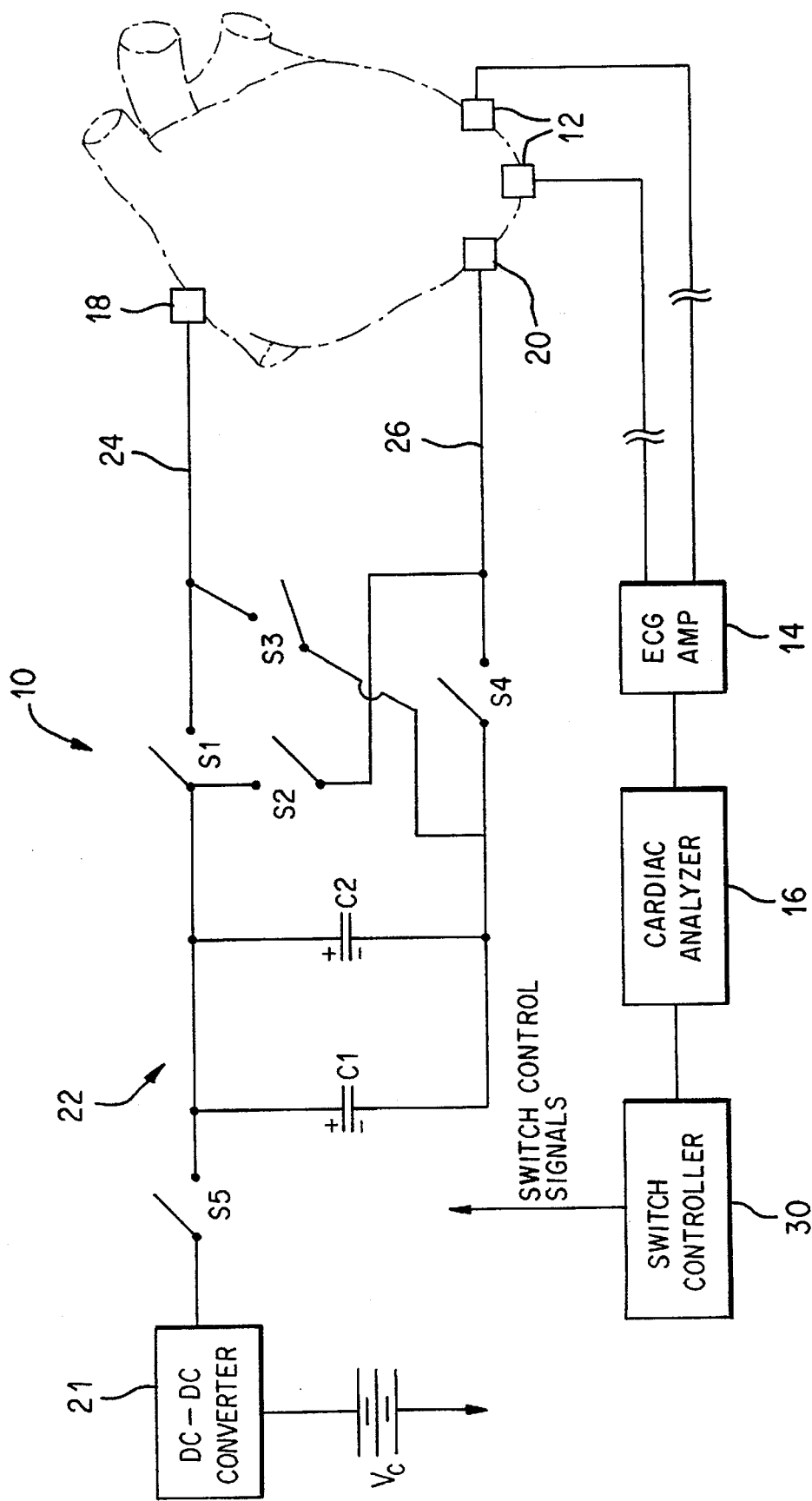
FIG. 4 is a schematic diagram illustrating the implantable defibrillation system according to a first embodiment of the present invention.

FIG. 4 illustrates the defibrillation system according to the first embodiment, which is generally shown at 10. The system 10 includes sensing electrodes 12 and circuitry for amplifying and analyzing the cardiac rhythm, in the form of an ECG amplifier 14 and a cardiac analyzer 16. The cardiac analyzer 16 determines when the heart is in a condition requiring a defibrillation (or cardioversion) shock and issues a control signal, causing the shock to be delivered to the heart via electrodes 18 and 20. The system 10 (as well as system 10' to be described hereinafter) represents an implantable or external defibrillation system. In an implantable system, electrodes 18 and 20 may be implanted on or about the heart, one may be subcutaneous, and each may comprise one or more electrode, though only one is shown for each. In the case of an external defibrillator, the circuitry may be disposed external to the body of a patient but connect with implantable electrodes. Alternatively, the external unit may connect with at least two cutaneous electrodes placed on the body.

The thrust of the present invention lies in the pulse generator circuitry, which is generally shown at 22. The pulse generator circuitry includes capacitors C1 and C2 connected in parallel. The capacitors C1 and C2 are charged by the voltage supply Vc via a DC-DC converter 21, and are connected to the electrodes 18 and 20 via lead lines 24 and 26. A plurality of switches S1–S4 are provided between the capacitors C1 and C2 and the lead lines 24 and 26. Preferably, capacitors C1 and C2 are 250 microFarads each, but may be in the range of 100–800 microFarads. The overall capacitance therefore is the sum of the capacitance of capacitors C1 and C2, which in the preferred embodiment is 200 to 1600 microFarads, but at least 200 microFarads or greater.

A switch controller 30 is provided to control the switches S1–S5, for controlling the charge and discharge of the capacitors C1 and C2. In general, the switch controller 30 controls the switches so that a biphasic waveform is generated from the discharge of the capacitors C1 and C2.

Figure 5:
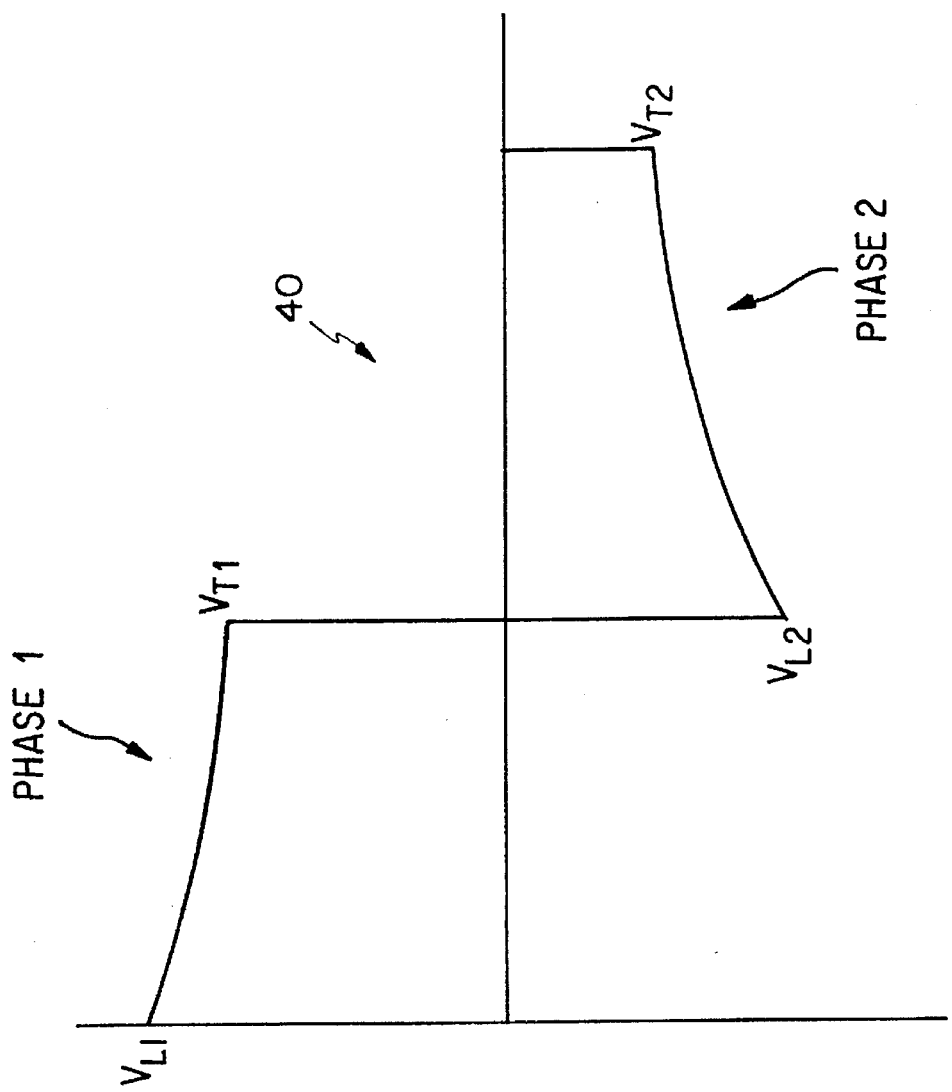
FIG. 5 is a diagram of a biphasic waveform generated by the pulse generator of the implantable defibrillation/cardioversion system according to the present invention.

With reference to FIGS. 4 and 5, the method by which the biphasic waveform 40 is generated will be described. The capacitors C1 and C2 are charged via the voltage supply Vc, by closing the switch S5. This may be controlled by the switch controller 30, or the cardiac analyzer 16. Once charged, the switch controller generates phase 1 of the waveform by closing switches S1 and S4, and opening switches S2 and S3. This connects the capacitors C1 and C2 with positive polarity to lead lines 24 and 26. The discharge waveform for phase 1 will slowly decay from a leading edge voltage VL1 to a trailing edge voltage VT1. The decay from VL1 to VT1 will be slow because the time constant for the circuit will be large, due to the sum of the capacitances of capacitors C1 and C2.

For the second phase of the waveform, the switch controller 30 opens switches S1 and S4 and closes switches S2 and S3, thereby connecting capacitors C1 and C2 to lead lines 24 and 26 with a polarity opposite to that of phase 1. Similar to phase 1, the discharge waveform for phase 2 decays at a rather slow rate from the leading edge voltage VL2 to the trailing edge voltage VT2. The magnitude of the leading edge voltage of phase 2, VL2, is equal to the magnitude of the trailing edge voltage VT1 of phase 1.

Preferably, the duration of the waveform shown in FIG. 5 is 20–40 msec, with the first phase consuming 60 percent of the total duration. In addition, the trailing edge voltage VT1 of the first phase is preferably larger than fifty percent of the leading edge voltage VL1, giving a low tilt shape to the waveform.

Figure 6:
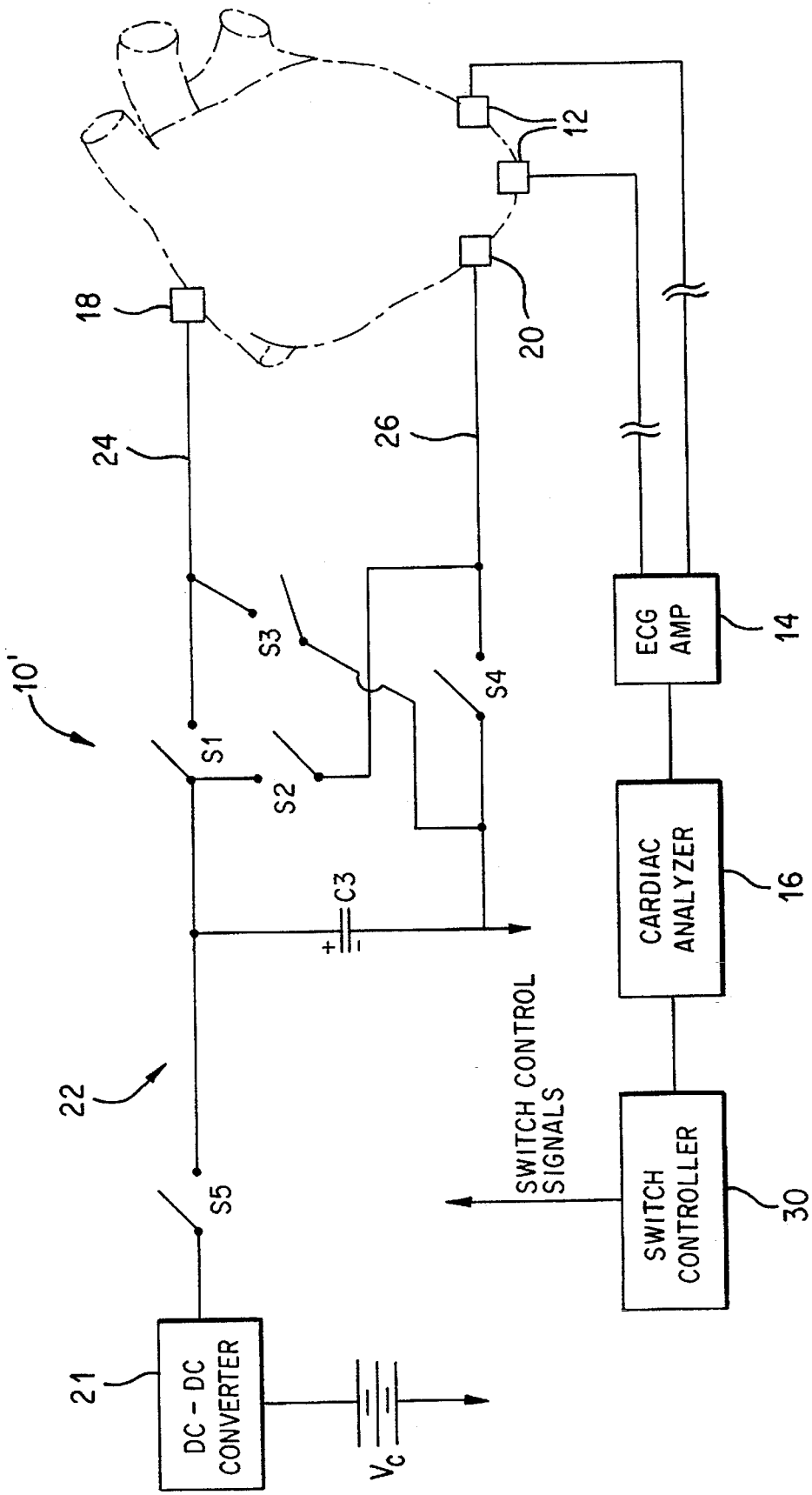
FIG. 6 is a schematic diagram illustrating the implantable defibrillation system according to a second embodiment of the present invention.

FIG. 6 illustrates the defibrillation system 10' according to the second embodiment of the present invention. Rather than two capacitors connected in parallel, a single high capacitance bipolar capacitor C3 is used. Alternatively, two capacitors connected in series may be used. Preferably, the capacitance of capacitor C3 is about 640 microFarads and need be charged to 360 volts, as opposed to conventional devices which use 125 microFarad aluminum electrolytic capacitors charged to 780 volts. A capacitor in the range of 200–1600 microFarads is appropriate, depending on application requirements, but preferably at least 200 microFarads. The lower voltage needed to charge the capacitor C3 simplifies the design of the pulse generator circuitry. This allows switches to be used with lower voltage and current ratings. Switches with lower ratings are more readily available, and reliability is improved if peak voltages and currents are reduced.

The operation of the system 10' with capacitor C3 is the same as for system 10. However, the capacitor C3 may provide an additional functional advantage. Specifically, because capacitor C3 is a low leakage bipolar capacitor, it can sustain charge longer than conventional smaller capacitors, without substantial leakage. Therefore, the capacitor C3 may be charged prior to a tachyarrhythmia detection and discharged immediately upon detection of a tachyarrhythmia, thus speeding up the response time of an implantable defibrillator (or cardioverter). For example, the capacitor C3 may retain charge for more than one day prior to a discharge, i.e. that less than ten percent of the original stored energy drains in one day. Additionally, by virtue of its large capacitance, multiple shocks can be delivered without recharging the capacitor.

The biphasic waveform according to the present invention appears to have several advantages over known defibrillation/cardioversion waveforms. By lengthening waveform duration, peak currents and voltages are decreased. Consequently, tissue damage caused by the peak voltage of the first phase can be minimized, and post-shock sensing of the heart is thereby improved. Because peak voltage and current are lower with the longer duration waveform, the output circuitry can be simplified and made more robust. These benefits are achieved with little or no increase in energy requirements.

The biphasic waveform according to the present invention can be generated using constant tilt or constant duration methods. One could also use constant duration for one phase and constant tilt for the other. In addition, system impedance could be determined and, based on that measurement, a constant duration or constant tilt system be automatically selected.

The foregoing description is intended by way of example only and is not intended to limit the present invention in any way except as set forth in the following claims.

What is claimed is:

1. A system for generating a defibrillation waveform including a defibrillator and an electrode structure, the system comprising:

a single capacitor having a capacitance of at least 200 microfarads;

means for charging said capacitor to a maximum voltage of less than 400 volts;

switch means for connecting said capacitor to said electrode structure; and switch control means for controlling said switch means to connect said capacitor to said electrode structure for discharge via said electrode structure in a first polarity for a first phase of a biphasic waveform, and to connect said capacitor to said electrode structure in a polarity opposite said first polarity for a second phase of said biphasic waveform;

the first phase having duration equal to or greater than said second phase, the total duration of the first and second phases being at least 15 milliseconds, a trailing edge voltage of said first phase being greater than fifty percent of a leading edge voltage of the first phase and the biphasic waveform having a fixed tilt so as to produce a fixed low tilt biphasic waveform.

2. The system of claim 1, wherein the capacitor has a capacitance of 200–1600 microFarads.

3. The system of claim 1, wherein said first and second phases have a total duration of 15–80 msec.

4. The system of claim 1, wherein said system includes an implantable housing for containing said capacitor, said charging means, said switch means, and said switch control means.

5. The system of claim 4, wherein the electrode structure comprises one or more electrodes adapted to be implanted on or about the heart and one or more electrodes adapted to be implanted subcutaneously.

6. The system of claim 1, wherein the system is adapted to be partially implantable, the defibrillator being adapted to be an external defibrillator, and wherein the electrode structure comprises at least two electrodes adapted to be implanted on or about the heart.

7. The system of claim 1, wherein the system is adapted to be partially implantable, the defibrillator being adapted to be an external defibrillator, and wherein the electrode structure comprises one or more electrodes adapted to be implanted on or about the heart and one or more electrodes adapted to be implanted subcutaneously.

8. The system of claim 1, wherein the system is adapted to be partially implantable, the defibrillator being adapted to be an external defibrillator, and wherein the electrode structure comprises at least two cutaneous electrodes adapted to be placed on the body.

* * * * *